United States Patent [19]

Collier

[11] Patent Number: 4,989,600
[45] Date of Patent: Feb. 5, 1991

[54] TANNING POD

[76] Inventor: Joseph M. Collier, 1365 Stuart St., Green Bay, Wis. 54301

[21] Appl. No.: 394,670

[22] Filed: Aug. 16, 1989

[51] Int. Cl.$^5$ .............................................. A61N 5/00
[52] U.S. Cl. ........................................ 128/372; 5/421; 128/373; 128/376
[58] Field of Search ............... 128/372, 376, 395, 346, 128/371, 377, 24.1, 24.2, 33, 200.12, 200.13, 373; 250/504 H; 600/21; 5/421, 423

[56] References Cited

U.S. PATENT DOCUMENTS

| 2,493,328 | 1/1950 | Wardyak | 128/372 |
| 3,908,666 | 9/1975 | Osborne | 128/372 |
| 4,277,855 | 7/1981 | Poss | 128/371 |
| 4,379,588 | 4/1983 | Speice | 128/372 |
| 4,424,598 | 1/1984 | Cilma | 4/524 |
| 4,441,220 | 4/1984 | Peterson | 128/376 |
| 4,525,884 | 7/1985 | Tolley | 128/376 |
| 4,856,520 | 8/1987 | Bilicki | 128/372 |

FOREIGN PATENT DOCUMENTS 214397 3/1987 European Pat. Off. ............ 128/395

Primary Examiner—Edward M. Coven
Assistant Examiner—Mark S. Graham
Attorney, Agent, or Firm—Richard C. Litman

[57] ABSTRACT

A tanning pod for use outdoors includes a body shell of curved configuration and provided with a transparent dome encompassing a majority of the extent of the pod and tapering to the front thereof. A bed within the pod is tiltable in a forward direction while a motive device is operable to rotate the pod relative an underlying support pedestal. A self-contained climate control system permits maintenance of desired temperature conditions within the pod regardless of the outside weather. Consoles adjacent the bed are provided with control panels allowing selective tilting of the bed and rotary displacement of the pod along with regulation of the climate control system as well as radiotape player devices. Current for operation of the pod and associated accessories may be supplied from a source of conventional AC power or alternatively, from attached or adjacent solar cells.

11 Claims, 2 Drawing Sheets

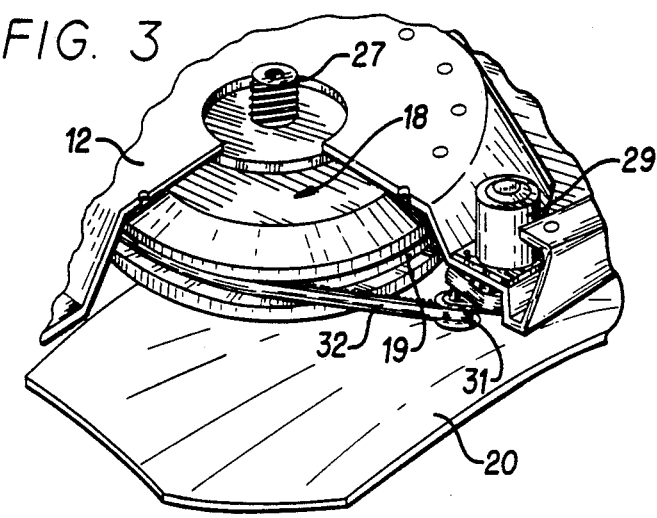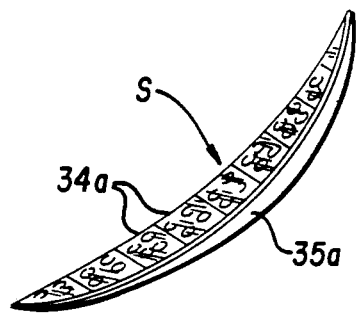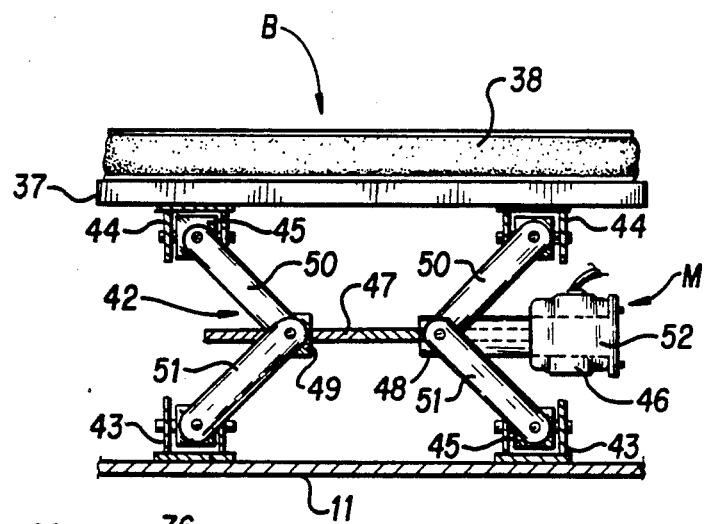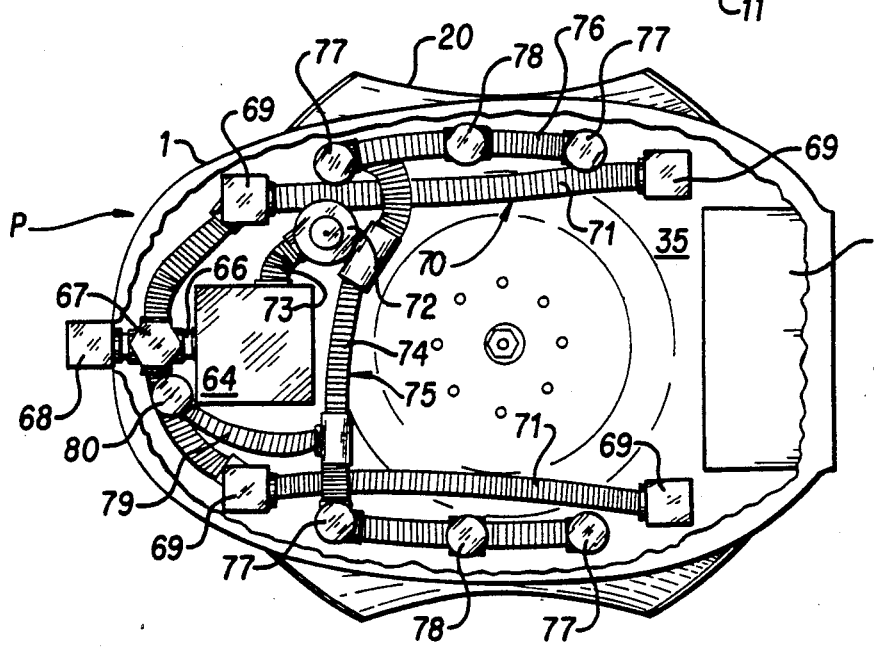

TANNING POD

FIELD OF THE INVENTION

This invention relates generally to recreational apparatus and more particularly, to an improved vessel serving as a tanning pod, usable by one or more persons to obtain a suntan regardless of the season or temperature of the outside air.

BACKGROUND OF THE INVENTION

With the noticeable increase in the amount of free time now available to so many persons and the heightened interest in the pursuit of recreational and outdoor activities, the need is recognized for means to facilitate and improve the enjoyment of such pastimes. In the case of sun bathing, such activity was long available only during the summer season and then, often only when one had ready access to an appropriate facility, such as a beach or poolside. Even during the warmer months of the year, sunbathing directly in the open air may be restricted due to windy conditions. Recently, suntanning salons have become quite popular. These facilities comprise indoor rental accommodations wherein patrons repose upon cushioned mats while being exposed to radiant lamps. Such arrangements fall far short of providing a tanning environment whereby one may obtain a natural suntan or merely enjoy the warmth of the sun, in an outdoor location and at any time of the year and, additionally, can present a measure of danger. It is well recognized that UV radiant energy lamps can readily lead to overexposure in a relative short period of time and precaution must be taken to shield the eyes during such exposure. Also, the resultant artificial tan is unlike that as obtained from natural sunlight. The present invention seeks to respond to the need for an apparatus which is usable in the outdoors to allow occupants to enjoy the sun's natural energy at any time of the year. The apparatus is self-contained and provides a controlled environment along with numerous enhancements furthering the users' enjoyment.

DESCRIPTION OF THE RELATED ART

Numerous devices have been proposed to accommodate persons seeking enjoyment from either natural or artificial sunlight. Design U.S. Pat. No. 279,313 issued to Tolley depicts a contoured sun bed encapsulated by a fully transparent canopy. An example of a solarium comprising an upright enclosure defining adjacent, interconnected dressing and tanning rooms will be found in Design U.S. Pat. No. 268,054 issued to Charette. U.S. Pat. No. 4,277,855 issued to Poss illustrates a portable sauna comprising a spherical housing containing climate control mechanisms. The improvements offered by the instant invention are seen as a definite advancement over the teachings of the above referenced prior art.

SUMMARY OF THE INVENTION

By the present invention, an improved capsule-like apparatus is provided allowing one or more persons to enjoy suntanning regardless of the season of the year or the ambient temperature. An elongated pod adapted to be located outdoors includes a transparent dome encompassing a major extent of the body shell of the apparatus. The shell is supported upon a pedestal and incorporates a motor drive by which users may selectively rotate the shell about the pedestal. A bed within the pod is provided with a motorized tilt mechanism by which the user may alter the inclination of the bed, independent of the rotation of the pod. To allow all-weather enjoyment of the pod, self-contained climate control means are included. Actuation of all motors and the climate control means is accomplished from control panels contained in two consoles within the pod, on either side of the bed, with power being supplied either from an external source of conventional current or, from attached or adjacent solar cells.

Accordingly, one of the objects of the present invention is to provide an improved tanning pod including a body shell containing a tiltable bed and which is selectively rotatable about a fixed pedestal.

A further object of the present invention is to provide an improved tanning pod including an elongated body shell having a transparent dome encompassing a majority of the expanse of the shell, with the dome curved downwardly toward the front of the pod.

Another object of the present invention is to provide an improved tanning pod including a shell body provided with a displaceable bed therein with adjacent controls permitting selective tilting of the bed.

Still another object of the present invention is to provide an improved tanning pod including a domed body shell containing a bed therein along with a self-contained climate control system operable from within the pod.

Another object of the present invention is to provide an improved tanning pod including a domed shell having an adjustable bed therein bounded by consoles provided with control panels operable to vary the inclination of the bed, rotate the pod, regulate the climate within the pod and actuate a music system.

A further object of the present invention is to provide an improved tanning pod including a body shell having upper and lower portions with a floor therebetween and provided with a tiltable bed atop the floor and motor means beneath the floor operable to selectively rotate the pod relative a fixed pedestal.

Another object of the present invention is to provide an improved tanning pod including a body shell containing a shiftable bed with motor means for rotating the shell and tilting the bed with the motor means being powered either from an external source of conventional current or solar cells associated with the pod.

With these and other objects in view which will more readily appear as the nature of the invention is better understood, the invention consists in the novel combination and assembly of parts hereinafter more fully described, illustrated and claimed with reference being made to the attached drawings.

BRIEF DESCRIPTION OF THE DRAWINGS

FIG. 3 is a fragmentary, top perspective view illustrating details of the pod rotary drive mechanism, with the bearing ring and its support plate removed for purposes of clarity;

FIG. 4 is an end elevation of the bed tilting mechanism, taken along the line 4—4 of FIG. 2;

FIG. 5 is a top plan view of the duct system disposed within the lower body shell and which provides for climate control within the pod; and FIG. 6 is a perspective view of a solar collector panel optionally associated with the pod.

Similar reference characters designate corresponding parts throughout the several figures of the drawings.

DESCRIPTION OF THE PREFERRED EMBODIMENT

Figure 1:
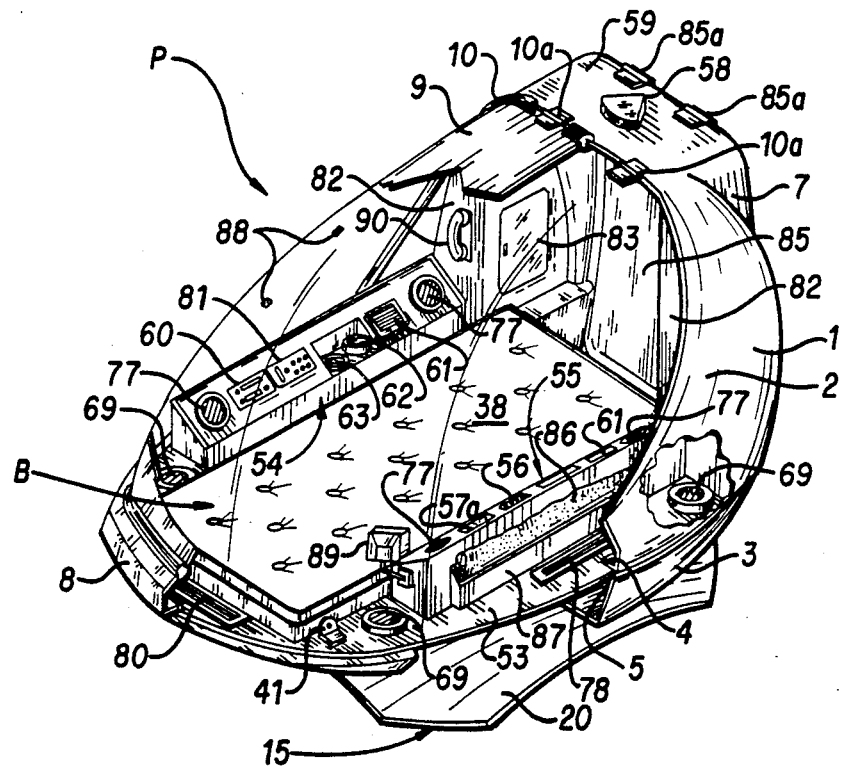
FIG. 1 is a fragmentary, top perspective view of the tanning pod of the invention.
Figure 2:
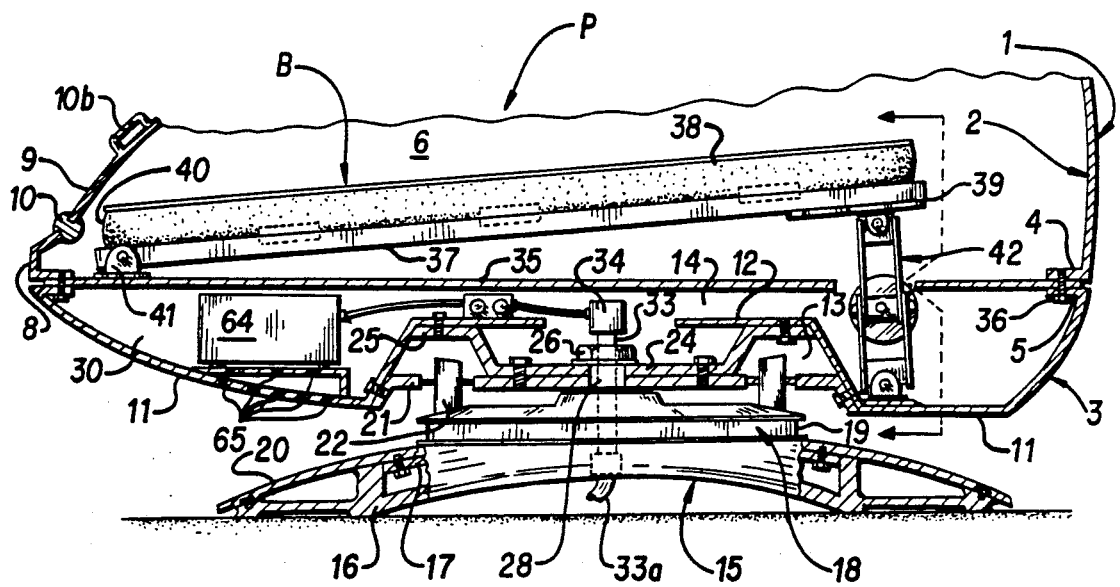
FIG. 2 is a partial side elevation, in section, of the pod shown in FIG. 1.

Referring now to the drawings, particularly FIGS. 1 and 2, the present invention relates to a modular structure comprising a pod or capsule, generally designated P. This pod will be seen to be formed by a body shell 1 having an upper portion 2 joined to a bottom portion 3, along mating, planar edges or flanges 4 and 5. The shell portions 2,3 may be constructed of any suitable lightweight material such as aluminum or synthetic plastics and which are readily formed or molded to provide the elongated, contoured configuration of the body 1. Preferably, the body 1 is formed to provide an occupant compartment 6 therein having its maximum height in the area adjacent the rear 7 of the body shell 1 and with the body upper portion 2 curved both inwardly and downwardly therefrom, toward the body front 8.

A significant portion of the surface area of the upper shell portion 2 is formed by a dome 9 constructed of any suitable transparent composition preferably, synthetic plastics. Quite obviously, the dome material may be tinted or otherwise treated to alter the transmission of certain wavelength rays from the sun. For example, with pods P as used near beaches in Florida, where one can expect to encounter quite warm temperatures and bright sunlight throughout the year, the dome 9 may be treated to reduce both visible light and infrared waves passing into the compartment 6. A unitary mounting-seal member 10 may be used to attach the periphery of the dome 9, in a weathertight manner, to the upper shell portion 2.

The dome 9 will be seen to present a bubble configuration and the seal member 10 may either provide a permanent attachment of the dome to the pod body portion 2 or, alternatively, permit opening of the dome to allow entrance and exit from the pod interior. In the latter instance, hinge members 10a may be used to pivotally attach the top edge of the dome 9 to the body shell portion 2, while a handle 10b offers ready means for raising and lowering the dome.

The body shell 1 is completed by the lower shell portion 3 which will be seen from FIG. 2 to define a vertical extent substantially less than that of the upper portion 2 and generally comprises a bottom wall 11 extending from the body front 8 to the body rear 7. This bottom wall 11 is provided with an upwardly displaced center section 12 forming a recess 13 which communicates with the interior compartment 6 through a central opening 14.

The cavity or recess 13 provides accommodation for structure to be described herebelow and which serves to support and angularly displace, the body shell 1 relative a pedestal assembly 15. This assembly 15 includes a base plate 16 of polygonal or annular configuration having a central, top section 17 to which is affixed a drive ring 18. The outer periphery of the drive ring 18 is provided with a belt-receiving groove 19 while a mask or cover 20 overlies the otherwise exposed peripheral portion of the base plate 16. The pod body shell 1 is supported upon the pedestal assembly 15 by means of a bearing ring 21 comprising a substantially planar plate containing a plurality of tapered bearing elements 22 consisting of tapered rollers or more preferably, tapered roller bearings, each having its axis of rotation radially aligned with respect to the center of the bearing ring 21 as shown in FIG. 2. The outer edge 23 of the bearing ring is suitably affixed to the lower body shell 3 so as to contain the structure of the bearing ring 21 within the confines of the shell recess 13.

To enhance the attachment of the body shell 1 to the pedestal assembly 15, a support plate 24 is removably attached to the bearing ring 21 and includes a vertically offset peripheral portion 25 attached to the displaced section 12 of the lower shell portion 3. In this manner, multiple attachment points between the pod shell and bearing ring are provided to increase stability of the mounted pod. Final retention of the shell is achieved upon application of a nut 26 about a bored, threaded hub 27 projecting upwardly from the drive ring 16 and freely passing through enlarged openings 28 in the stacked bearing ring 21 and support plate 24.

FIG. 3 most clearly illustrates the manner of producing angular or rotary movement of the pod shell 1 relative the stationary pedestal assembly 15. As will be seen in this drawing figure, a reversible motor 29 is mounted within the cavity 30 of the lower shell portion 3, to one side of the pedestal mounted drive ring 18. This motor 29 is provided with a driven output wheel or pulley 31 disposed in the same horizontal plane as the adjacent drive ring groove 19. A flexible drive belt 32 is respectively sheaved about the groove 19 and driven pulley 31 such that upon actuation of the motor 29, the pulley 31 traverses the belt 32 in either direction to move the body shell 1 in an arcuate manner atop the stationary pedestal assembly 15. Electrical power to operate the motor 29 and other components yet to be described, is supplied from a suitable source and directed through a fixed conduit 33 leading upwardly through the drive ring hub 27 to a rotatable junction box 34 located within the lower shell portion cavity 30.

As shown in FIG. 2, a wiring cable 33a may be passed into the pod from beneath the stationary pedestal 15. The current for operating the various electrical components may be supplied from local or remote power sources and may comprise conventional AC current or electrical energy as generated by solar cells. In the latter instance, solar cell panels may be situated adjacent the pod 1 (not shown) or affixed to any suitable surface of the pod. FIG. 6 illustrates a typical configuration of a solar cell array S containing a plurality of cell assemblies 34a mounted on a support wing 35a suitably affixed to any portion of the pod.

The foregoing description relates to the construction of the pod shell 1, its support upon the pedestal assembly 15 and the motor means for selectively rotating the pod body. Details regarding the contents of the occupant compartment 6 and supporting accessories may now be described.

From FIGS. 1 and 2 it will be noted that a planar floor plate 35 substantially isolates the user compartment 6 from the lower shell portion cavity 30. For ease of assembly and repair, this floor plate 35 is preferably sandwiched between the mating flanges 4 and 5 of the two shell portions 2,3 and secured by means of appropriate fasteners 36. Overlying the majority of the extent of this floor plate is a bed B comprising a substantially rigid, planar frame 37 in turn supporting a topmost mattress or pad 38. To accommodate alteration of the inclination of the bed B, the frame is mounted for raising and lowering of its first or head end 39 with respect to the opposite, second or foot end 40. This latter end is connected to pivot blocks 41 permitting only pivoting of the bed about a fixed horizontal axis while a tilt mechanism 42 is disposed beneath the first bed end 39.

FIG. 4 most clearly illustrates the construction of the tilt mechanism 42 which comprises a dual scissors apparatus supported upon the bottom wall 11 of the lower shell portion 3 and acting upon the undersurface of the bed frame 37 adjacent its first end 39. Included are a pair of u-shaped brackets 43,44 respectively affixed to the bottom wall 11 and bed frame 37, each of which contains a knuckle 45 mounted for pivotal movement about a transverse axis. Intermediate the two pairs of brackets 43,44 is a motor assembly M including a reversible tilt motor 46 having an output comprising a screw shaft 47 provided with left and right hand threaded portions at opposite ends thereof. Mounted about the respective threaded portions are threaded blocks 48,49, with one block 48 being fixedly attached relative the motor 46. From FIGS. 2 and 4 it will be apparent that a pair of links 50 have their opposite ends respectively pivotally connected to each of the two brackets 44 while similar pairs of links 51 are connected to each of the two brackets 43. A motor mount 52 rigidly interlocks the motor 46 relative the one threaded block 48 to preclude axial and angular movement of the motor as a result of thrust produced during its operation. In this manner, it will be understood that upon actuation of the motor 46, the screw shaft 47 thereof is rotated to thereby cause the two threaded blocks 48,49 to either move toward one another or apart, depending upon the direction of rotation of the motor 46. This action produces a contraction or extension of the pivotal links 50-51 to respectively lower or raise the first end 39 of the bed B.

From the foregoing it will be appreciated that motor means have been described for accomplishing both lateral or arcuate, rotary movement of the pod shell 1 as well as alteration of the inclination or tilt of the bed B within the occupant compartment 6. Ready means are provided within the pod enclosure to enable the user to actuate the respective motors for producing the above movements. From FIG. 1 it will be seen that the bed mattress 38 is preferably of rectangular configuration and since both the shell portions 2,3 and the floor plate 35 define a smoothly curved configuration, it follows that a substantial clearance 53 will exist laterally of each side of the mattress 38. First and second consoles 54,55 are provided within the clearances 53,53, each extending the majority of the length of the bed B. Included in at least one such console is a movement control panel 56 electrically connected to the two described motors 29 and 46 whereby, a user of the invention, while reposing upon the mattress 38, has ready access to switches 57 actuating both the angular rotation of the pod P as well as the inclination or tilt of the bed.

With the above construction, a user of the invention may follow the sun if desired. That is, by actuating the motor 29, the nose or body front portion 8 of the pod can be periodically turned toward the available sunlight. Additionally, by altering the inclination of the bed B through use of the appropriate switches 57 controlling the tilt motor 46, one may manipulate the relative angle between the plane of their body and that of the current elevation of the sun. Alternatively, means may be included to automatically track the elevation and path of the sun's movement. For example, computer software and hardware (not shown) may be activated and which is programmed according to the user's location and the day of the year, to automatically follow the sun's path. In other instances, a sensor 58 may be employed on the roof 59 of the body shell 1 and which detects the most brilliant source of available light and appropriately actuates the two motors 29, 46 to align the pod and tilt the bed accordingly. Such alignment also will position any solar collectors S in the most ideal position to receive the maximum radiation.

Entertainment, in the nature of radio or taped music, is provided by means of a radio/tape player unit 60 in one console 54 or 55 and which plays back through at least one speaker 61 in each of the two consoles. Other accessories lending to the comfort of the user are included in the consoles, such as at least one ashtray 62 and cup or glass receptacle 63.

A most important aspect of the subject tanning pod is the inclusion of self-contained climate control means. FIGS. 1 and 5 most clearly illustrate such control means the majority of which is located within the confines of the lower shell portion cavity 30, laterally and forwardly of the bearing ring 21. The heart of this control means comprises a small HVAC unit 64 which preferably comprises a heat pump and which may communicate with the ambient atmosphere through grill openings 65 (FIG. 2). Air, for circulation through the HVAC unit 64, is collected by an intake duct 66 with the source being either the outside air or that air existing within the pod compartment 6. In the former case, an intake control valve 67 is actuated to permit outside air to be drawn through an outside vent 68 while in the latter instance, the valve 67 is actuated to allow compartment air to be collected through a series of vents 69 in a return air system 70 including a duct 71 along each side of the pod. These vents 69 are preferably located in the floor plate 35, adjacent both ends of each console 54,55.

A blower 72, preferably acting as a suction device off the HVAC unit 64, by way of a duct 73, directs its output to a manifold duct 74 of a supply air system 75. Two lateral, supply air ducts 76,76 below or within the two lateral consoles 54,55 are connected to this manifold duct 74 and deliver air from a plurality of vents or outlets 77 on each console as well as a single floor mounted vent 78 between each console and the adjacent side of the body shell. Also, a forwardly directed duct 79 leads from the manifold duct 74 and delivers air from a vent 80 in the floor plate 35 adjacent the forward nose 8 of the pod. Each of these vents may obviously include rotary and/or pivotal vaned members to allow the user to alter the volume and/or direction of the supplied air therefrom.

To enable the user to regulate the HVAC unit 64 and maintain the desired conditions within the compartment 6, a climate control panel 81 is provided on one of the consoles 54. In this manner, one may enjoy the benefits of the tanning pod P throughout the year and in all climates with the source of electricity for operating the HVAC unit 64 being supplied either through the same conduit 33 delivering current for operation of the tilt and rotation motors 46, 29 or, the solar collector S. As in the operation of an automobile, the plurality of console and floor mounted vents may be employed to deliver outside air, heated or cooled air for maintenance of the desired temperature within the pod compartment 6, as well as air for defrosting or drying any frost or moisture forming on the dome 9.

The consoles include a digital clock timer 57a by which a user may set an alarm to define periods of exposure.

As will be seen from the view of FIG. 1, the two rear corners of the body shell 1 are provided with an enclosure 82 having an access door 83, enabling the user to store various articles such as books, tapes, towels and the like. As these enclosures 82 are rearward of the bed B and dome 9 they do not interfere with the movement of the user nor their view through the dome. As shown in FIG. 5, the floor plate 35 is provided with a cutout 84 at the rear thereof. The forward portion of this cutout provides clearance for the tilt mechanism 42 while the remainder allows persons entering and leaving the pod to use the lower shell portion bottom wall 11 as a floor, thereby presenting the maximum headroom in this rear area of the pod. A door 85 formed in the body rear 7, is preferably hinged along its top as at 85a and provides ready access to the pod compartment. Although but one mattress is shown in the drawings herein, the pod of this invention may be readily adapted to accommodate two users merely by enlarging the lateral dimension thereof. In such a case, a single wider bed may be provided or, two adjacent beds each with independent tilt altering means (not shown).

To provide lateral privacy when desired, a flexible shroud 86 may be hung within the compartment 6. The shroud 86, normally stored, such as in housings 87 adjacent each console, is raised when used and hung by suitable means such as VELCRO tabs 88 on the interior of the dome 9. Other entertainment and convenience items such as the telephone 89 and TV 90 shown in FIG. 1 may be provided.

It is to be understood that the present invention is not limited to the sole embodiment described above, but encompasses any and all embodiments within the scope of the following claims.

I claim:

1. A tanning pod comprising;
a body shell including an upper portion defining an occupant compartment therewithin,
said body shell having a lower portion adjacent said upper portion, a horizontally and vertically fixed floor plate intermediate said shell upper and lower portions,
said body shell defining an elongated curved configuration having rear and front portions, said shell upper portion including a dome of transparent material extending downwardly from adjacent said rear portion to said front portion and encompassing a substantial area of said upper portion.
a pedestal assembly beneath said body shell,
motive means adjacent said body shell and pedestal assembly and operable to angularly displace said body shell relative said pedestal assembly,
a substantially fixed, longitudinal, rigid body support bed within said compartment mounted atop said floor plate and having opposite head and foot ends with said foot end adjacent said shell front portion, hinge means mounting said bed foot end to said floor plate,
vertical displacement means operable to raise and lower said bed head end to tilt said bed about said hinge means relative a horizontal plane and said body shell,
climate maintenance means including an HVAC unit disposed within said body shell, and
first, second, and third control means selectively operable by an occupant within said compartment respectively to operate said motive means, vertical displacement means and climate maintenance means.

2. A tanning pod according to claim 1 including,
consoles disposed within said compartment laterally of said bed, and
said control means mounted within said consoles.

3. A tanning pod according to claim 1 wherein,
said motive means includes a drive ring fixed relative said pedestal assembly,
a motor carried by said body shell and having driving means, and
means joining said driving means and drive ring, whereby
upon actuation of said motor, said body shell is rotatably displaced relative said pedestal assembly.

4. A tanning pod according to claim 1 wherein,
said climate maintenance means includes a plurality of ducts connected to said HVAC unit, and
vents within said compartment communicating with said ducts and adapted to pass return and supply air from and to said compartment, respectively.

5. A tanning pod according to claim 1 wherein,
said vertical displacement means comprises a scissors mechanism including a plurality of pivotal links beneath said bed head end, and
motor means operable to displace said links.

6. A tanning pod according to claim 1 including,
dome hinge means joining said dome to said body shell upper portion, whereby
said dome is pivotable to allow entrance and exit from said occupant compartment.

7. A tanning pod according to claim 1 including,
a solar cell array exterior of said occupant compartment adapted to supply current to operate said motive means.

8. A tanning pod according to claim 1 including,
a stowable flexible shroud within said dome, and
fastening means within said dome, whereby
said shroud is manipulatable from a stowed position to a use position where it may be engaged by said fastening means.

9. A tanning pod according to claim 1 wherein,
said motive means is disposed within said body shell lower portion.

10. A tanning pod according to claim 1 including,
a first door mounted within said body shell rear portion, and
a storage enclosure within said compartment and having a second door, said storage enclosure disposed adjacent said first door.

11. A tanning pod according to claim 10 wherein,
said first door includes a top edge, and
door hinge means attaching said door top edge to said body shell rear portion, whereby
said first door is pivotally operable along said top edge to permit entrance and exit from said occupant compartment.

* * * * *